United States Patent [19]

Elton et al.

[11] 4,205,185

[45] May 27, 1980

[54] PROCESS FOR PREPARING RACEMIC 4-HYDROXYPHENYLGLYCINE

[75] Inventors: Michael J. Elton, Newcastle; Arthur Jackson, Washington; John W. Harrison, Newcastle upon Tyne, all of England

[73] Assignee: Sterling Drug Inc., New York, N.Y.

[21] Appl. No.: 938,475

[22] Filed: Aug. 31, 1978

Related U.S. Application Data

[63] Continuation-in-part of Ser. No. 449,363, Mar. 8, 1974, abandoned, which is a continuation-in-part of Ser. No. 160,152, Jul. 6, 1971, abandoned.

[51] Int. Cl.$^2$ ............................................. C07B 20/00
[52] U.S. Cl. .................................................. 562/444
[58] Field of Search ................................. 562/401, 444

[56] References Cited

U.S. PATENT DOCUMENTS

| 2,824,128 | 2/1958 | Dexter | 562/443 X |
| 3,000,888 | 9/1961 | Biekert | 562/444 X |

OTHER PUBLICATIONS

Chemical Abstracts I, (Decombe), vol. 27, 2941, (1933).
Grillot et al., J. Amer. Chem. Soc., 67, 1968–1969 (1945).
Chemical Abstracts II, vol. 60, 1627e,f, (1964).
March, Advanced Organic Chemistry: Reactions, Mechanisms and Structures, McGraw-Hill, New York, (1968), pp. 424, 670–672.

*Primary Examiner*—Norman Morgenstern
*Assistant Examiner*—Vera C. Clarke
*Attorney, Agent, or Firm*—Frederik W. Stonner; B. Woodrow Wyatt

[57] ABSTRACT

A process for the preparation of racemic 4-hydroxyphenylglycine, in which phenol, glyoxylic acid (or a salt thereof) and ammonia are reacted together to produce the desired 4-hydroxyphenylglycine.

7 Claims, No Drawings

PROCESS FOR PREPARING RACEMIC 4-HYDROXYPHENYLGLYCINE

CROSS-REFERENCES TO RELATED APPLICATIONS

This appliction is a continuation-in-part of copending application Ser. No. 449,363, filed Mar. 8, 1974, abandoned, in turn a continuation-in-part of application Ser. No. 160,152, filed July 6, 1971, abandoned.

BACKGROUND OF THE INVENTION

1. Field And Object Of The Invention

The invention relates to a process for preparing racemic 4-hydroxyphenylglycine having the following structural formula:

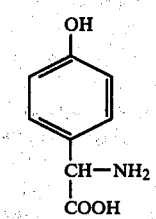

4-Hydroxyphenylglycine is useful as an intermediate in the preparation of derivatives of penicillanic acid.

It is an object of the invention to provide a novel process for the preparation of 4-hydroxyphenylglycine.

A concomitant object of the invention is to provide such a process which is capable of yielding 4-hydroxyphenylglycine in a comparatively pure state, i.e., having an assay of at least 97 percent, and in good yield.

A further concomitant object of the invention is to provide such a process from which the formed 4-hydroxyphenylglycine can be isolated in a comparatively pure state and in good yield directly from the reaction mixture using standard procedures thus precluding the need for subsequent tedious separation and purification procedures.

2. Description of the Prior Art

Aminomethylation can be broadly characterized as consisting of the condensation of an aldehyde and ammonia, or a primary or secondary amine, either in the free base or salt form, with a compound having a reactive (acidic) hydrogen, resulting in electrophilic substitution of the latter compound. In the case where phenol is the reactive-hydrogen compound it is well known that the directing influence of the hydroxyl group in electrophilic substitutions is ortho/para and on a statistical basis ortho, i.e., 2-position, substitution would be expected to predominate over para, i.e., 4-position, substitution. That ortho substitution does in fact predominate in the aminomethylation of phenol is documented in the art [for example see Decombe, Chem. Abs., 27, 2941 (1933); Grillot et al., J. Amer. Chem. Soc., 67, 1968–69 (1945)]. Furthermore, it has previously been found that a similar aminomethylation type of reaction, namely the reaction of phenol, glyoxlic acid and a diamine at a pH between 8 and 10 gives rise to an appropriate 2-hydroxyphenylglycine derivative (Dexter, U.S. Pat. No. 2,824,128)—that is to say, the substitution of the phenolic nucleus occurs at the 2 (or ortho) position rather than the 4 (or para) position. A literature report which appears contrary, that is, appears to contradict art-established evidence that aminomethylation of phenol occurs predominantly at the ortho position, is Abdullaev et al., Chem. Abs. 60, 1627 (1964), wherein it is reported that a yield of 92% para-hydroxybenzylamine was obtained on condensation of paraformaldehyde and ammonia with phenol. However, when we repeated this reaction, following the identical procedure described by Abdullaev et al., very little, if any, para-hydroxybenzylamine was obtained as determined by means of standard thin layer chromatography technique by comparison of the reaction mixture with an authentic sample.

SUMMARY OF THE INVENTION

The present invention is based upon the unexpected discovery that 4-hydroxyphenylglycine, in racemic form, and not 2-hydroxyphenylglycine, is obtained as the predominant hydroxyphenylglycine in a process wherein phenol, glyoxylic acid (or a salt thereof) and ammonia are mixed together and reacted at a pH of 4 or greater and at comparatively low reaction temperatures. Thus it was discovered that of the total hydroxyphenylglycine formed in the process of the invention, less than 10 percent is 2-hydroxyphenylglycine and more than 90 percent is 4-hydroxyphenylglycine.

The formation of the 2-hydroxyphenylglycine isomer in less than 10 percent yield and of the 4-hydroxyphenylglycine isomer in greater than 90 percent yield is not only surprising, for the reasons discussed hereinbefore, but is a distinct advantage since, if the 2-hydroxy isomer were formed in substantially higher proportion relative to the 4-hydroxy isomer, subsequent tedious separation of the 2-hydroxy isomer and the desired 4-hydroxy isomer would be required which would render the process uneconomical.

Thus this invention provides a process for the preparation of racemic 4-hydroxyphenylglycine, wherein, based on the total amount of hydroxyphenylglycine formed, less than about 10 percent is 2-hydroxyphenylglycine and greater than about 90 percent is 4-hydroxyphenylglycine, the process comprising reacting in an aqueous medium and at a pH of 4 or greater:
(a) ammonia;
(b) phenol; and
(c) glyoxylic acid;
in a molar ratio of a:b:c of about 4:1.25:1 to about 19:13:1, at a temperature in the range of about 20° C. to about 75° C., and for a period of time sufficient to effect condensation of a, b and c to form the hydroxyphenylglycine.

DETAILED DESCRIPTION INCLUSIVE OF THE PREFERRED EMBODIMENTS

The process of the invention is conveniently carried out under aqueous conditions, i.e., in an aqueous medium, (although other media such as alcohol, e.g., methanol, or media comprising combinations of water and water-miscible solvents, can be used), employing about 50% (w/w) aqueous glyoxylic acid, phenol, and concentrated aqueous ammonia.

An excess of both phenol and ammonia is employed such that the amounts present are greater than those required stoichiometrically to react with the glyoxylic acid, the amount of ammonia being present in sufficient excess to provide a reaction media having an alkaline pH. If desired, the pH of the reaction can be adjusted to lower values, but not below about pH 4, by addition of an appropriate amount of an acid. For this purpose any non-oxidizing mineral acid is suitable such as, for example, hydrochloric acid, sulfuric acid and phosphoric acid. Preferably the reaction is carried out in the approximate pH range of from about 4 to about 12.

Although for maximum yield of 4-hydroxyphenylglycine it is better to use high excesses of both phenol and ammonia, in large scale preparations it is preferred that the reaction should be effected using from about 1.25 to 8.5 moles of phenol and from about 4.0 to 18.0 moles of ammonia per mole of glyoxylic acid, an optimum value being about 2.4 moles of phenol and about 6.0 moles of ammonia per mole of glyoxylic acid. Conveniently, there should be from about 1.5 to 6.0 moles per mole of phenol, an optimum value being about 2.5 moles of ammonia per mole of phenol.

The glyoxylic acid can be employed in the form of a salt thereof—such as the ammonium salt or an alkali metal salt like the sodium salt—and is preferably added to the reaction mixture over a prolonged period rather than all at once. Thus as used herein, the term glyoxylic acid means glyoxylic acid and salts thereof.

The rate of reaction is of course temperature dependent and although the reaction proceeds satisfactorily at, for example, 20° C., the reaction time is shortened as reaction temperature is increased. On the other hand, when the reaction temperature is too high, yields are reduced due to decomposition. Therefore, while reaction temperatures in the range of about 20° C. to 75° C. may be employed, it was found that an optimum temperature is in the range of 40° C. to 60° C. with 45° C. being the preferred reaction temperature.

The desired 4-hydroxyphenyglycine can be isolated from the reaction mixture by most of the well-known methods for isolating analogous compounds.

In a particularly preferred procedure, the reaction mixture is extracted with a water-immiscible solvent to remove excess phenol and the aqueous phase is treated with sodium metabisulfite to prevent discoloration and charged into concentrated hydrochloric acid, while keeping the temperature below 95° C. The aqueous phase is then adjusted to a pH of 6.5 to 7 and the resulting precipitated 4-hydroxyphenylglycine is collected and washed with water and methanol.

Alternatively, after extraction of excess phenol, the aqueous phase is concentrated by distillation to remove excess ammonia and then is treated with concentrated hydrochloric acid. Addition of sufficient acid to adjust the pH to 6.5 to 7 results in precipitation of the 4-hydroxyphenylglycine. Acidification with about one mole excess of the acid results in a solution of 4-hydroxyphenylglycine which is treated with charcoal and basified with concentrated aqueous ammonia to pH 6.5 to 7 to precipitate the 4-hydroxyphenylglycine. Acidification with a large excess of the acid results in precipitation of 4-hydroxyphenylglycine hydrochloride which can be collected. The hydrochloride salt can then be dissolved in water, treated with charcoal if desired, and the solution adjusted to pH 6.5 to 7 by addition of base to precipitate the 4-hydroxyphenylglycine.

The solvent used in the isolation procedure for extracting excess phenol can be any water-immiscible solvent for phenol which will not react with the 4-hydroxyphenylglycine. Such solvents are for example, isopropyl acetate (preferred), ethylene dichloride and isopropyl ether.

The 4-hydroxyphenylglycine prepared by the process of this invention is in the form of a racemic mixture (the α-carbon atom is asymmetric). If desired, this racemic mixture can be resolved using appropriate resolution techniques to give the separate optical isomers.

The following examples are illustrative of particularly preferred techniques employed in the process of this invention.

EXAMPLE 1

Preparation via the hydrochloride

An aqueous solution of glyoxylic acid (92 g. glyoxylic acid monohydrate (1 mole) in 92 ml. water) is added over 11 hours to a stirred solution of phenol (800 g.) in concentrated (0.880) aqueous ammonia (700 ml.), the temperature being maintained at 45° C. throughout the addition. The reaction mixture is stirred for a further 1 hour at 45° C., and then cooled to 20° C. Excess phenol is extracted with two portions of isopropyl ether (1×600 ml., 1×300 ml.). The aqueous solution is then concentrated by distillation (preferably under reduced pressure) to a volume of about 200 ml.

Concentrated hydrochloric acid (75 ml.) is added, followed by water, to give a total volume for the solution of 300 ml. A further portion of concentrated hydrochloric acid (300 ml.) is then added, and the solution is cooled to 0° to 5° C. The precipitated 4-hydroxyphenylglycine hydrochloride is collected by filtration (yield 88 g., 43.2% of theoretical), and dissolved in water (160 ml.). The aqueous solution is treated with decolorising charcoal at 50° C. for 15 minutes, and after filtration the pH is adjusted to 7 at 85° to 95° C. with concentrated aqueous ammonia. The mixture is then cooled to 0° to 5° C., and 4-hydroxyphenylglycine is collected by filtration, washed free of inorganic salts with water, and dried. Yield 60.0 g. (35.9% of theoretical) as an off-white powder, assay 97% to 99%; m.p. 220°–221° C.

EXAMPLE 2

Preparation without intermediate isolation

4-Hydroxyphenylglycine can be isolated directly from the reaction mixture of Example 1 without intermediate isolation of the hydrochloride salt. However, the product is discolored and of low assay.

The procedure described in Example 1 is repeated. After removal of excess phenol by extraction with isopropyl ether, the reaction mixture is concentrated to low volume (300 ml.) by distillation. The reaction mixture is cooled to 0° to 5° C. and filtered, preferably after dilution with methanol (300 ml.) to improve filtration efficiency. The 4-hydroxyphenylglycine is dried. Yield 92.2 g., assay 85.0% (55.1% of theoretical); m.p. 220°–221° C.

EXAMPLE 3

Alternative preparation without intermediate isolation

Isolation of 4-hydroxyphenylglycine directly from the reaction mixture, without intermediate isolation of the hydrochloride salt, is much improved by the following technique.

The procedure of Example 1 is followed except that the 92 g. glyoxylic acid monohydrate in 92 ml. water is first neutralised to pH 7 with concentrated aqueous ammonia before addition to the phenol and concentrated ammonia. Further, after removal of excess phenol from the reaction mixture, the aqueous layer is concentrated by distillation until excess ammonia is removed, the mixture is then acidified with concentrated hydrochloric acid, and the resulting solution is treated with decolorising charcoal. After filtration, the pH of the solution is adjusted to 6.5 to 7 with concentrated aqueous ammonia and cooled, and the precipitated 4-hydroxyphenylglycine is removed by filtration. The product is washed with water until free of inorganic salts, and is then dried. Yield 65 g. (39% of theoretical); m.p. 220°-221° C.

EXAMPLE 4

Additional preparation without intermediate isolation

Direct isolation can be achieved more efficiently and effectively than shown in Examples 2 and 3 is the phenol is left in the reaction mixture until after filtration of the 4-hydroxyphenylglycine.

A 50% w/w solution of aqueous glyoxylic acid (88.8 g.) is added over 6 hours to a stirred solution of phenol (145 g.) in 0.88 ammonia (200 ml.) and water (200 ml.). The temperature is maintained at 45° C. throughout the addition. The reaction mixture is left for a further hour at 45° C., after which the pH is brought to 7 with concentrated hydrochloric acid (about 180 ml.), keeping the temperature below 60° C.; this precipitates the 4-hydroxyphenylglycine. The whole is heated to 90° C. and cooled back to 20° C. (this improves filtration), and filtered. The wet cake is reslurried in water (100 ml.) to remove the phenol, filtered and washed with methanol (30 ml.) to remove any final traces of phenol, to give 43 g. of 4-hydroxyphenylglycine, assay 97%. Yield 41.6%; m.p. 220°-221° C.

EXAMPLE 5

Additional preparation without intermediate isolation

The procedure described in Example 3 is repeated, except that after removal of excess phenol with isopropyl ether, the reaction mixture is concentrated by distillation until a heavy precipitate of 4-hydroxyphenylglycine is observed and the pH of the mixture is in the range of 8.0 to 9.0. The mixture is brought to 50° C., and concentrated hydrochloric acid (about 125 ml.) is added until the precipitate redissolves. The solution is treated successively with two portions of 5 g. of decolorising charcoal, 1 g. filter aid and 0.5 g. sodium hydrosulphite, and is filtered after each treatment. The pH of the filtrate is then adjusted to 6 to 7 at 85° to 95° C. with concentrated aqueous ammonia (about 90 ml.), and after cooling to 0° to 5° C. the precipitated 4-hydroxyphenylglycine is removed by filtration, washed with cold water until free of inorganic salts, and dried. The yield of 4-hydroxyphenylglycine is 63.5 g. (38% of theoretical), assay 97% to 99% as an off-white powder; m.p. 220°-221° C.

EXAMPLE 6

Preparation using minimal amount of phenol

The amount of phenol used can be reduced to a 2-molar excess with only slight decrease in yield. The proportions of isopropyl ether used for extraction of excess phenol are similarly reduced with the smaller phenol charge.

A solution of glyoxylic acid monohydrate (92 g.) in water (92 ml.) is neutralised to pH 7 with about 90 ml. concentrated aqueous ammonia, and added over 11 hours at 45° C. to a mixture of phenol (300 g.) and concentrated aqueous ammonia (700 ml.). The reaction mixture is then heated for a further 1 hour at 45° C., cooled to 20° C., and excess phenol extracted with two portions of isopropyl ether (1×300 ml., 1×150 ml.). The aqueous solution is concentrated to low volume by distillation, and 4-hydroxyphenylglycine hydrochloride precipitated by the addition of excess concentrated hydrochloric acid. The yield of 4-hydroxyphenylglycine hydrochloride is 85.5 g. (42.1% of theoretical).

Evaporation of the isopropyl ether extracts leaves a residue of phenol (184 g.), assay 99.4% (recovery 71% of theoretical).

EXAMPLE 7

Use of recovered phenol

The phenol residue resulting from distillation of the isopropyl ether extracts may be used directly in the synthesis without further purification.

The procedure described in Example 1 is repeated using 300 g. of recovered phenol residues. The yield of 4-hydroxyphenylglycine hydrochloride is 84.5 g. (41.5% of theoretical).

EXAMPLE 8

Preparation adding glyoxylic acid in stages

The solution of glyoxylic acid is preferably added over a period of time. The optimum addition time is 11 hours at a reaction temperature of 45° C., followed by a further period of 1 hour at 45° C.

The procedure is Example 1 is repeated. Addition of glyoxylic acid solution over a 6 hour reaction period gave 72.5 g. (35.6% of theoretical); addition over a 12 hour period gave 85.5 g. (42.1% of theoretical); addition over 24 hours gave 86.5 g. (42.6% of theoretical).

EXAMPLE 9

Preparation using glyoxylic acid salt

Glyoxylic acid is added as a solution of the ammonium or sodium salt in water, rather than as the free acid. A solution of the ammonium salt is preferable to the sodium salt as, in the latter case, precipitation of sodium chloride is a complicating factor during isolation of 4-hydroxyphenylglycine hydrochloride. Addition of excess caustic to the reaction mixture does not increase the yield.

The procedure described in Example 1 is repeated, using 300 g. phenol, 300 ml. concentrated aqueous ammonia in 400 ml. water, and 148 g. of 50% aqueous glyoxylic acid to which a solution of 40 g. of sodium hydroxide in 100 ml. of water has been added. The yield of 4-hydroxyphenylglycine hydrochloride is 76.6 g. (37.7% of theoretical).

The procedure described in Example 1 is then repeated using 300 g. phenol, 300 ml. concentrated aqueous ammonia in 400 ml. water, and 148 g. of 50% aqueous glyoxylic acid to which 120 ml. concentrated aqueous ammonia has been added. The yield of 4-hydroxyphenylglycine hydrochloride is 81.3 g. (40% of theoretical).

EXAMPLE 10

Temperature Dependence

The reaction is preferably carried out at a temperature in the range 40° to 60° C., 45° C. being an optimum with respect to yield and time of reaction. At lower temperatures the time for completion of reaction is extended (e.g. 12 hours at 45° C., 22 hours at 35° C., 70 hours at 25° C.). At higher temperatures the reaction rate is fast, but is accompanied by increased product decomposition and by-product formation.

The procedure described in Example 1 is repeated. The solution of glyoxylic acid is added over 1 hour at 75° C., and the reaction mixture then heated for a further 1 hour at 75° C. The yield of 4-hydroxyphenylglycine hydrochloride is 58.0 g. (28.6% of theoretical).

EXAMPLE 11

Use of various amounts of phenol and ammonia

The yield of product, and to a lesser extent the reaction rate, are highly dependent on the total charge of ammonia and phenol. Product yield is increased as the ratio of phenol and ammonia to glyoxylic acid is increased.

The procedure described in Example 1 is repeated using 400 g. phenol, 350 ml. concentrated aqueous ammonia, and 92 g. (1 mole) glyoxylic acid monohydrate, the reactants being mixed and heated for 7 hours at 45° C. The yield of 4-hydroxyphenylglycine hydrochloride is 55.0 g. (27.0% of theoretical).

Using 800 g. phenol, 700 ml. concentrated aqueous ammonia, and 92 g. glyoxylic acid monohydrate, the yield of 4-hydroxyphenylglycine hydrochloride is 84.7 g. (41.7% of theoretical). Using 1,200 g. of phenol, 1,050 ml. concentrated aqueous ammonia, and 92 g. of glyoxylic acid monohydrate, the yield of 4-hydroxyphenylglycine hydrochloride is 98.0 g. (48.2 of theoretical).

EXAMPLE 12

Continuous precipitation

Precipitation of 4-hydroxyphenylglycine throughout the reaction may be effected by including hydrochloric acid from the beginning.

0.88 Ammonia (200 ml.) is added to a solution of 50% w/w aqueous glyoxylic acid (88.8 g.) and water (100 ml.). The pH is brought 7 with concentrated hydrochloric acid (about 180 ml.), keeping the temperature below 20° C., and this solution is added to a phenol solution (145 g.) in water (100 ml.). The whole is left for 5 hours, keeping the temperature between 20° and 30° C.; it is then stirred at room temperature for 72 hours, keeping the pH between 6.5–7 by addition of concentrated hydrochloric acid. The formed 4-hydroxyphenylglycine is then filtered off, reslurried in water (100 ml.), filtered and washed with methanol to give 42 g. 4-hydroxyphenylglycine, assay 97%. Yield 40.8%.

EXAMPLE 13

Large scale production

A solution (1000 kg.) of 50% w/w of aqueous glyoxylic acid is diluted with 700 l. of water and added over a period of 6 hours to a solution consisting of 1600 liters of water, 1070 kg. of phenol (100%) and 2100 liters of concentrated (0.880) aqueous ammonia while the temperature of the reaction is maintained between 45° to 50° C. After addition is completed, stirring is continued for 30 minutes. The reaction mixture is extracted two times with 1200 liters each time of isopropyl acetate. The aqueous phase is separated, charged with 12 kg. of sodium metabisulfite (to prevent discoloration), and added to 2050 liters of concentrated hydrochloric acid while maintaining the temperature below 95° C. The pH is then adjusted to 6.5 to 7 and the aqueous phase is cooled to 20° C. The resulting precipitate is filtered and washed with water and methanol to yield 400 kg. (35.5% yield) of 4-hydroxyphenylglycine; assay > 98%; m.p. 219°–221°.

Using GLC (gas-liquid chromatography), it was determined that of the total amount of hydroxyphenylglycine formed employing the procedure of Example 13, less than 10 percent is the 2-hydroxy isomer and greater than 90 percent is the 4-hydroxy isomer; it was also determined, using GLC, that the isolated 4-hydroxyphenylglcyine (assay > 98%) contains less than 0.8 percent of the 2-hydroxy isomer.

We claim:
1. A process for the preparation of racemic 4-hydroxyphenylglycine, wherein, based on the total amount of hydroxyphenylglycine formed, less than about 10 percent is 2-hydroxyphenylglycine and greater than about 90 percent is 4-hydroxyphenylglycine, which comprises reacting in an aqueous medium and at a pH of 4 or greater:
   (a) ammonia;
   (b) phenol; and
   (c) glyoxylic acid;
in a molar ratio of a:b:c of about 4:1.25:1 to about 19:13:1; at a temperature in the range of from about 20° C. to about 75° C.; and for a period of time sufficient to effect condensation of a, b and c to form the hydroxyphenylglycine.

2. The process of claim 1 wherein the molar ratio of a:b is from about 1.5:1 to about 6:1.

3. The process of claim 2 wherein the molar ratio of a:b:c is about 5.8:1.7:1.

4. The process of claim 3 wherein the temperature is in the range of from about 45° C. to 50° C.

5. The process according to claim 2 wherein the molar ratio of a:b is from about 1.5:1 to about 2.5:1.

6. The process according to claim 5 wherein the molar ratio of a:b:c is about 6:2.4:1.

7. The process according to claim 6 wherein the temperature is about 45° C.

* * * * *